United States Patent
Kane et al.

(10) Patent No.: US 7,645,795 B2
(45) Date of Patent: Jan. 12, 2010

(54) METHOD FOR TREATING AMYOTROPHIC LATERAL SCLEROSIS

(75) Inventors: Patricia Kane, Millville, NJ (US); Edward Kane, Millville, NJ (US)

(73) Assignee: BodyBio, Inc, Millville, NJ (US)

( * ) Notice: Subject to any disclaimer, the term of this patent is extended or adjusted under 35 U.S.C. 154(b) by 885 days.

(21) Appl. No.: 10/946,601

(22) Filed: Sep. 21, 2004

(65) Prior Publication Data

US 2005/0019423 A1 Jan. 27, 2005

(51) Int. Cl.
- *A01N 37/02* (2006.01)
- *A61K 31/23* (2006.01)
- *A01N 37/06* (2006.01)
- *A61K 31/225* (2006.01)
- *A61K 31/22* (2006.01)

(52) U.S. Cl. .................. 514/552; 514/547; 514/549

(58) Field of Classification Search ................ 514/552, 514/547, 549
See application file for complete search history.

(56) References Cited

U.S. PATENT DOCUMENTS

| | | | | |
|---|---|---|---|---|
| 4,221,784 A | 9/1980 | Growdon et al. | ............ | 424/199 |
| 5,780,489 A | 7/1998 | Brooks | ........................ | 514/369 |
| 6,379,666 B1 * | 4/2002 | Tobinick | .................... | 424/134.1 |
| 6,572,899 B1 | 6/2003 | Gorsek | ........................ | 424/732 |
| 7,384,981 B2 * | 6/2008 | Kiliaan et al. | ................ | 514/558 |
| 2005/0227915 A1 * | 10/2005 | Steffan et al. | .................. | 514/9 |
| 2006/0069157 A1 * | 3/2006 | Ferrante | ........................ | 514/557 |

OTHER PUBLICATIONS

Roy G. Cutler, et al. "Evidence That Accumulation of Ceramides and Cholesterol Esters Mediates Oxidative Stress-Induced Death of Motor Neurons in Amyotrophic Lateral Sclerosis", *Annals of Neurology*, 52:448-457 (2002).

John Kelemen, et al. "Lecithin is Not Effective in Amyotrophic Lateral Sclerosis", *Neurology*, 32:315-316 (1982).

Zheng Cui, et al. "Phosphatidylcholine and Cell Death", *Biochimica et Biophysica Acta 1585*, pp. 87-96 (2002).

Randy Linde, et al. "Hypokalemia and Amyotrophic Lateral Sclerosis", *JAMA*, 246(17):1899-1900 (1981).

* cited by examiner

*Primary Examiner*—Sreeni Padmanabhan
*Assistant Examiner*—Kara R McMillian

(57) ABSTRACT

The administration of nutritional supplements such as phosphatidylcholine; linoleic acid and alpha linolenic acid in an approximately 4:1 (v/v) ratio; and mineral supplements provides an effective method for the treatment of ALS. Subjects presenting with symptoms indicative of ALS can therefore be treated with these nutritional supplements to inhibit progression of ALS. Subjects at risk for developing ALS can also be treated with these nutritional supplements to delay the onset of ALS symptoms.

1 Claim, No Drawings

METHOD FOR TREATING AMYOTROPHIC LATERAL SCLEROSIS

FIELD OF THE INVENTION

This invention relates to the treatment of amyotrophic lateral sclerosis with nutritional supplements, in particular with phosphatidylcholine, essential fatty acids and minerals.

BACKGROUND OF THE INVENTION

Amyotrophic lateral sclerosis (ALS), also known as Lou Gehrig's disease, is a progressive, fatal neurological disease affecting as many as 30,000 Americans, with 5,000 new cases occurring in the United States each year. In ALS, the motor neurons in the brain and spinal cord that control voluntary movement degenerate over time. The loss of these motor neurons causes the muscles under their control to weaken and waste away, leading to paralysis and death. The mean survival time for ALS patients is 2-5 years post-diagnosis. ALS typically strikes in mid-life, and men are about one-and-a-half times more likely to develop the disease than women. There is no cure for ALS, and present therapies provide only supportive care during the inevitable decline of the patient.

ALS occurs in both sporadic (SALS) and familial (FALS) forms. Recent genetic and biochemical studies implicate free radical toxicity and glutamate excitotoxicity as possible causes of SALS. About 10% of all ALS patients are familial cases, of which 20% have mutations in the superoxide dismutase 1 (SOD1) gene (formerly known as Cu, Zn-SOD). An abnormally functioning SOD1 enzyme may therefore play a pivotal role in the pathogenesis and progression of FALS (Rosen et al., 1993, *Nature* 362: 59; Siddique et al., 1991, *N. Engl. J. Med.* 324:1381).

More than 50 point mutations of the human SOD1 gene have been found in patients with FALS. Most of the mutations occur at regions which encode the SOD1 active site, so that the enzymes produced from the mutant SOD1 genes have reduced activity. The function of the SOD1 enzyme is to remove oxygen radicals from the cellular environment. Motor neurons which produce mutant SOD1 therefore show increased oxygen radical generation. It is believed that the increased generation of oxygen free radicals, especially hydroxyl radicals, due to the presence of mutant SOD1 triggers in the sequence of events leading to motor neuron death in FALS. This hypothesis is supported by recent reports that transfection of neuronal precursor cells with mutant SOD1 results in increased production of hydroxyl radicals and enhanced rate of cell death by apoptosis (Liu et al., 1999, *Radiat. Res.* 151:133).

The only approved drug for treatment of ALS is the glutamate-release antagonist riluzole, which extends the lifespan of ALS patients only by approximately 3 months. Thus, riluzole provides only a mild benefit to ALS patients. Moreover, riluzole evokes hepatic stress upon elevation of liver enzymes. It is poorly tolerated by a majority of patients.

The antibiotic minocycline has been reported to delay the onset and slow the progression of ALS symptoms in the "SOD1" mouse model of ALS, apparently by inhibiting apoptotic cell death in motor neurons. However, the effect of minocycline on SOD1 mouse survival is roughly equivalent to that of riluzole. Therefore, minocycline is not expected to significantly lessen ALS symptoms or lengthen the lifespan of ALS patients.

Clinical trials are underway to determine whether administration of creatine monohydrate increases muscle strength in ALS patients, and to determine whether insulin-like growth factor-1 (IGF-I) slows the progressive weakness in ALS patients. However, regulatory approval of these drugs for treatment of ALS is many years away, and in any case neither of these drugs are expected to provide more than a palliative effect.

What is needed, therefore, is a method of treating ALS which results in a reduction or reversal of symptoms, which significantly lengthens the lifespan of ALS patients, and which uses materials currently available for use in treatment of humans.

SUMMARY OF THE INVENTION

It has now been found that providing ALS patients with the nutritional supplement phosphatidylcholine, in combination with mineral and essential fatty acid supplements, relieves the symptoms of ALS and inhibits the progression of the disease. The invention therefore provides a method of treating ALS in a subject who has been diagnosed with ALS, comprising administering an effective amount of one or more compositions comprising phosphatidylcholine, and an effective amount of one or more compositions comprising linoleic acid and alpha linolenic acid in an approximately 4:1 (v/v) ratio. An effective amount of one or more compositions comprising mineral supplements is also administered to the subject being treated for ALS. The identity and amount of mineral supplements administered to the subject is individually determined for each subject according to that subject's nutritional status. In one embodiment, the subject being treated for ALS also receives glutathione administered intravascularly.

The invention also provides a method of treating a subject at risk for developing ALS in order to delay the onset of ALS symptoms, comprising administering to that subject an effective amount of one or more compositions comprising phosphatidylcholine, and an effective amount of one or more compositions comprising linoleic acid and alpha linolenic acid in an approximately 4:1 (v/v) ratio. An effective amount of one or more compositions comprising mineral supplements is also administered to the subject being treated for ALS. The identity and amount of mineral supplements administered to the subject is individually determined for each subject according to that subject's nutritional status. In one embodiment, the subject being treated for ALS also receives glutathione administered intravenously.

The invention also provides a pharmaceutical compositions (also called medicaments) for treating ALS or for delaying the onset of ALS symptoms. Pharmaceutical compositions are prepared using 1) one or more compositions comprising phosphatidylcholine; 2) one or more compositions comprising linoleic acid and alpha linolenic acid in an approximately 4:1 (v/v) ratio; and/or 3) one or more compositions comprising mineral supplements. The pharmaceutical compositions may be prepared to utilize at least one butyrate compound, and an oral electrolyte composition.

The invention further provides a kit for the treatment of ALS or for delaying the onset of ALS symptoms. The kit comprises instructions for treating ALS in a subject, or for delaying the onset of ALS symptoms in a subject, and one or more of the following components: 1) one or more compositions comprising phosphatidylcholine; 2) one or more compositions comprising linoleic acid and alpha linolenic acid; and 3) one or more compositions comprising mineral supplements. The kit may optionally comprise one or more butyrate compounds. The kit may optionally comprise an oral electrolyte composition. The latter maybe in concentrated form, for dilution by the user.

DETAILED DESCRIPTION OF THE INVENTION

The administration of phosphatidylcholine, linoleic acid and alpha linolenic acid in an approximately 4:1 (v/v) ratio, and mineral supplements provides an effective method for the treatment of ALS. A subject presenting with symptoms indicative of ALS can therefore be treated by the method of the invention to inhibit progression of ALS. A subject at risk for ALS can also be treated by the method of the invention to delay the onset of ALS symptoms.

As used herein, a "subject" is any mammal, in particular a primate, preferably a human, that 1) exhibits at least one symptom associated with ALS; 2) has been diagnosed with ALS; or 3) is at risk for developing ALS.

rated by reference. For example, the "El Escorial" criteria for the diagnosis of ALS require: (1) the presence of (a) evidence of lower motor neuron (LMN) degeneration by clinical, electrophysiological or neuropathologic examination; (b) evidence of upper motor neuron (UMN) degeneration by clinical examination; and (c) a progressive spread of symptoms or signs within a region or to other regions as determined by history or examination; and (2) the absence of (a) electrophysiological or pathological evidence of other disease processes that might explain the signs of LMN or UMN degeneration; and (b) neuroimaging evidence of other disease processes that might explain the observed clinical and electrophysiological signs. Typical LMN and UMN signs indicative of ALS are given in Table 1.

TABLE 1

Typical ALS lower motor neuron and upper motor neuron signs

| | Brainstem | Cervical | Thoracic | Lumbosacral |
|---|---|---|---|---|
| Lower motor neuron (LMN) signs weakness, atrophy, fasciculations | jaw, face palate tongue larynx | neck, arm, hand diaphragm | back abdomen | back, abdomen leg, foot |
| Upper motor neuron (UMN) signs pathologic spread of reflexes, clonus, etc. | clonic jaw, jerk gag reflex exaggerated snout reflex pseudo-bulbar features forced yawning pathologic DTR[1] spastic tone | clonic DTR Hoffman reflex pathologic DTR spastic tone preserved reflex in weak wasted limb | loss of superficial abdominal reflexes pathologic DTR spastic tone | clonic DTR extensor plantar response pathologic DTR spastic tone preserved reflex in weak wasted limb |

[1]Deep tendon reflex.

As used herein, a "subject at risk for developing ALS" includes subjects with a family history of ALS or who are susceptible to developing ALS. Subjects "susceptible to developing ALS" include those subjects testing positive for molecular markers indicative of or associated with ALS, such as any one of the known mutations in the SOD1 gene described in, for example, Deng et al., 1993, *Science*, 261: 1047-1051, the entire disclosure of which is herein incorporated by reference. One skilled in the art can readily identify subjects at risk for ALS.

One skilled in the art can also readily identify ALS symptoms in a subject, or diagnose ALS in a subject. The natural history of ALS is well documented (Munset T. L., 1992, The natural history of amyotrophic lateral sclerosis. In: *Handbook of Amyotrophic Lateral Sclerosis*, Smith R A (eds.), Chapter 2, pp. 39-63, Marcel Dekker, Inc.: New York, the entire disclosure of which is herein incorporated by reference). The presenting symptoms of ALS include muscle wasting or weakness of the hands or legs. Occasionally, cramps and fasciculations precede the common presenting symptoms. Bulbar symptoms consisting of dysartria or dysphagia typically appear as the disease progresses, but can also be the presenting complaints in some subjects.

Standard criteria for diagnosis of ALS have been established by the World Federation of Neurology, and is described in Brooks et al., "El Escorial revisited: revised criteria for the diagnosis of amyotrophic lateral sclerosis," *Amyotroph. Lateral. Scler. Other Motor Neuron Disord*. 2000 December; 1(5):293-9, the entire disclosure of which is herein incorpo- In addition to the "El Escorial" criteria for diagnosing ALS (Brooks et al., (2000), supra), one or more of the following standard clinical evaluations can be used to identify ALS symptoms or assess progress/prevention of ALS in a subject:

(1) Quantitative strength and functional markers. The TUFTS Quantitative Neuromuscular Examination (TQNE) is a well standardized, reliable, validated test to measure strength and function in ALS. The test involves measurement of maximum voluntary isometric contraction (MVIC) of eight muscle groups in the arms using a strain gauge tensiometer.

(2) Functional measures. The ALS Functional Rating Scale (ALSFRS) is an easily administered ordinal rating scale used to determine patient' assessment of their ability and independence for ten functional activities. Validity has been established by correlating ALSFRS scores with change in strength over time.

(3) Neuropathologic examination of muscle, peripheral nerve and other tissue biopsies. The presence of neuropathologic features such as chronic denervation/reinervation in affected muscle tissue, scattered hypertrophied muscle fibers, necrotic muscle fibers, inflammatory cell infiltration and giant axonal swellings in intramuscular nerves are all indicative of ALS. An overview of neuropathologic findings in patients with ALS is presented in, for example, A. Hirano (1996), "Neuropathology of ALS: an overview," *Neurology*, 47 (Suppl 2): S63-S66, the entire disclosure of which is herein incorporated by reference.

As discussed above, the progression of ALS in a subject diagnosed with ALS can be inhibited by treatment of a subject by the present methods. The present methods can also delay the onset of ALS in a subject at risk for the disease.

As used herein, the progression of ALS is "inhibited" when the spread of the disease to new anatomic segments or to new regions of the central nervous system slows or stops, or when the severity of at least one ALS symptom remains constant or is lessened. As used herein, the "severity of ALS symptoms remains constant" when there is no detectable change in the symptom over time, for example as evaluated by any standard ALS evaluation as described above. As used herein, the "severity of ALS symptoms is lessened" when the subject shows improvement of one or more symptoms, for example as measured by any standard ALS evaluation as described above.

As used herein, the onset of ALS symptoms is "delayed" if the first subjective, but clinically verifiable, symptom noticed by the patient occurs later than expected. For example, the onset of ALS symptoms is "delayed" in a subject when that subject has not reported any clinically verifiable ALS symptoms by the age at which family members who have ALS had already reported such symptoms. The onset of ALS symptoms is also considered to be "delayed" in a subject when that subject has not reported any clinically verifiable ALS symptoms by the average age at which individuals of the same age and gender, and who also have ALS, have already reported such symptoms.

In the practice of the present methods, an effective amount of one or more compositions comprising phosphatidylcholine (hereinafter "PC composition") is administered to a subject who has been diagnosed with, or who is at risk for developing, ALS. Any PC composition can be used, including compositions consisting essentially of phosphatidylcholine. Preferred PC compositions include Essentiale N™ 500 mg phosphatidylcholine IV solution, available from A. Natterman & Cie, GmbH (Cologne, Germany); PhosChol™ 100% phosphatidylcholine preparation, available from Nutrasal LLC (Oxford, Conn. USA); and E-Lyte PhosChol™ 100% phosphatidylcholine preparation available from E-Lyte, Inc. (Millville, N.J. USA).

The one or more PC compositions can be administered to the subject by any parenteral or enteral technique suitable for introducing the composition into the blood stream or gastrointestinal tract, including intravascular (e.g., intravenous and intraarterial) injection and oral administration. In a preferred embodiment, the one or more PC compositions are administered to the subject intravascularly. In a more preferred embodiment, the one or more PC compositions are administered to the subject orally and intravascularly.

As used herein, an "effective amount" of the one or more PC compositions is any amount sufficient to inhibit the progression of ALS, or to delay the onset of ALS symptoms, when administered in conjunction with linoleic acid and alpha linoleic acid in an approximately 4:1 ratio, and one or more compositions comprising mineral supplements. An effective amount of the one or more PC compositions can contain from about 0.5 to about 21 grams phosphatidylcholine, preferably from about 1 to about 15 grams phosphatidylcholine, more preferably from about 2 to about 7.5 grams phosphatidylcholine, and particularly preferably from about 3 to about 5 grams phosphatidylcholine. It is understood that total amount of the one or more PC compositions which represent the effective amount can be administered intravascularly, orally, or both.

One skilled in the art can readily determine an appropriate dosage regimen for administering the one or more PC compositions. For example, the one or more PC compositions can be administered once, twice or more daily, for one, two, three, four, five, six or seven days in a given week. The length of time that the subject receives a PC composition can be determined by the subject's physician or primary caretaker, according to need. Due to the chronic and progressive nature of ALS, it is expected that subjects will receive a PC composition according to the present methods for an indefinite period of time, likely for the rest of their lives.

In a preferred embodiment, one PC composition which contains about 500 mg phosphatidylcholine is administered to a subject intravenously twice or thrice daily for consecutive or non-consecutive days in a given week. Another PC composition, which contains from about 3.6 to about 7.2 grams phosphatidylcholine, is administered once or twice to the same subject daily by mouth.

In the practice of the present methods, one or more compositions comprising linoleic acid and alpha linolenic acid in an approximately 4:1 (v/v) ratio (hereinafter "EFA 4:1 composition") are administered to a subject who has been diagnosed with, or who is at risk for developing, ALS. It is understood that one or more compositions comprising linoleic acid, and one or more compositions comprising alpha linoleic acid, can be administered separately to a subject, as long as the ratio (v/v) of linoleic acid to alpha linolenic acid administered within a given time frame (e.g., 24 hours or less, preferably 12 hours or less, more preferably 6 hours or less, particularly preferably 4 hours or less) is approximately 4:1. The term "EFA 4:1 composition" therefore refers to one or more compositions comprising linoleic acid and one or more compositions comprising alpha linolenic acid, which are separately administered to a subject an approximately 4:1 (v/v) ratio of linoleic acid to alpha linolenic acid. The term "EFA 4:1 composition" also refers to a single composition comprising linoleic acid and alpha linolenic acid in an approximately 4:1 (v/v) ratio. Preferably, the EFA 4:1 composition used in the present methods is a single composition comprising linoleic acid and alpha linolenic acid in an approximately 4:1 (v/v) ratio.

Any commercially available preparation comprising (or consisting essentially of) linoleic acid and alpha linolenic acid, or mixtures of the two in an approximately 4:1 (v/v) ratio, can be used as the EFA 4:1 composition in the present methods. A mixture of cold pressed organic safflower or sunflower oil and flaxseed oil may be utilized to yield a 4:1 ratio of linoleic acid and alpha linolenic acid. A suitable EFA 4:1 composition is BodyBio Balance 4:1.TM. EFA oil available from E-Lyte, Inc. (Millville, N.J. USA).

The one or more EFA 4:1 compositions can be administered to a subject by any parenteral or enteral technique suitable for introducing the one or more EFA 4:1 compositions into blood stream or the gastrointestinal tract. In a preferred embodiment, the one or more EFA 4:1 compositions are administered to the subject by mouth.

As used herein, an "effective amount" of the one or more EFA 4:1 compositions is any amount sufficient to inhibit the progression of ALS, or to delay the onset of ALS symptoms, when administered in conjunction with one or more PC composition and one or more compositions comprising mineral supplements. An effective amount of the one or more EFA 4:1 compositions can be from about 10 mls (about 2 teaspoons) to about 100 mls (about 7 tablespoons), preferably about 15 mls (about 1 tablespoon) to about 80 mls (about 5 tablespoons), more preferably about 30 mls (about 2 tablespoons) to about 60 mls (about 4 tablespoons).

One skilled in the art can readily determine an appropriate dosage regimen for administering the one or more EFA 4:1 compositions. For example, the one or more EFA 4:1 compositions can be administered once, twice or more daily, for one, two, three, four, five, six or seven days in a given week. The length of time that the subject receives the one or more EFA 4:1 compositions can be determined by the subject's physician or primary caretaker, according to need. Due to the chronic and progressive nature of ALS, it is expected that subjects will receive the one or more EFA 4:1 compositions according to the present methods for an indefinite period of time, likely for the rest of their lives.

In a preferred embodiment, from about 30 mls to about 60 mls (about 2 to about 4 tablespoons) of the one or more EFA 4:1 compositions are administered to a subject by mouth, once daily.

In the practice of the present methods, an effective amount of one or more compositions comprising mineral supplements (hereinafter "mineral compositions") are also administered to subject who has been diagnosed with, or who is at risk for developing, ALS. A single mineral composition can be administered to the subject, or two or more mineral compositions can be administered separately. It is understood that mineral compositions can be administered separately to a subject, as long as the compositions are administered within a given time frame (e.g., 24 hours or less, preferably 12 hours or less, more preferably 6 hours or less, particularly preferably 4 hours or less). Preferably, the one or more mineral compositions for use in the present methods comprise biologically available forms of potassium, magnesium, zinc, copper, chromium, manganese, molybdenum, selenium and iodine, or any combination thereof, although the mineral compositions can comprise other minerals in biologically available form.

The compositions comprising mineral supplements can be administered to a subject by any parenteral or enteral technique suitable for introducing the compositions into the blood stream or gastrointestinal tract. In a preferred embodiment, the compositions comprising mineral supplements are administered to the subject by mouth.

Any commercially available composition or compositions comprising (or consisting essentially of) one or more biologically available minerals can be used as a mineral composition in the present methods. Suitable mineral compositions include solid multi-mineral preparations, or the E-Lyte Liquid Mineral™ set #1-8 (separate solutions of biologically available potassium, zinc, magnesium, copper, chromium, manganese, molybdenum and selenium) or #1-9 (separate solutions of biologically available potassium, zinc, magnesium, copper, chromium, manganese, molybdenum, selenium and iodine), both available from E-Lyte, Inc. (Millville, N.J. USA).

The effective amount of the one or more mineral compositions administered to a subject inhibits the progression of ALS, or delays the onset of ALS symptoms, when administered in conjunction with one or more PC compositions and the one or more EFA 4:1 compositions. As used herein, an "effective amount" of the one or more mineral compositions refers to both the identity and amount of each mineral administered to a subject. This effective amount of the one or more mineral compositions is determined for each subject according to that subject's needs and nutritional status, based on a nutritional evaluation of the subject. Suitable techniques for performing a nutritional evaluation of a subject include standard blood tests to determine serum mineral and electrolyte levels, and subjective evaluations such as the E-Lyte, Inc. "taste test" for determining mineral deficiencies. The E-Lyte, Inc. "taste test" for determining mineral deficiencies is described below in the Examples.

After determining the effective amount of the one or more mineral compositions for administration to the subject, one skilled in the art can readily determine the dosage regimen for administering the one or more mineral compositions. For example, the mineral compositions can be administered once, twice or more daily, for one, two, three, four, five, six or seven days in a given week. Preferably, the one or more mineral compositions are administered to the subject twice a day, for seven days in a given week. The length of time that the subject receives the one or more mineral compositions can be determined by the subject's physician or primary caretaker, according to need. Due to the chronic and progressive nature of ALS, it is expected that subjects will receive the one or more mineral compositions according to the present methods for an indefinite period of time, likely for the rest of their lives.

In a preferred embodiment, a subject being treated according to the present methods also receives intravascular (e.g., intravenous) glutathione. The term "glutathione" is typically used as a collective term to refer to the tripeptide L-gamma-glutamyl-L-cysteinylglycine in both its reduced and dimeric forms. Monomeric glutathione is also known as "reduced glutathione" and its dimer is also known as oxidized "glutathione", "glutathione disulfide" or "diglutathione". As used herein, reduced glutathione will be called "glutathione".

For example, a subject can receive from about 1 to about 3 grams of glutathione, preferably about 1.5 to about 2.8 grams glutathione, more preferably about 1.8 to about 2.4 grams glutathione, once, twice or more daily, for one, two, three, four, five, six or seven days a week. In one preferred embodiment, the subject receives from about 1.8 to about 2.4 grams intravenous glutathione twice daily, for four consecutive or non-consecutive days in a given week. In another preferred embodiment, the glutathione is administered as an intravenous "fast push" over three to five minutes.

Any commercially available composition comprising (or consisting essentially of) glutathione can be used in the present methods. Suitable compositions comprising glutathione include the glutathione preparations from Wellness Health and Pharmaceuticals (Birmingham, Ala. USA), Medaus Pharmacy (Birmingham, Ala. USA) and Roche Tationile 600 (Milan, Italy).

In a preferred embodiment, a subject treated according to the present methods also receives one or more butyrate compounds, preferably orally. By "butyrate compound" is meant a compound comprising a salt or ester of butyric acid. Butyrate compounds include, for example, calcium butyrate, magnesium butyrate, sodium butyrate, sodium phenyl butyrate, and combinations thereof. The butyrate compound may be administered orally, preferably in capsule form. Solid dosages may range from about 3 grams to about 12 grams daily, more preferably from about 3 grams to about 6 grams. For example, calcium magnesium butyrate may be administered as 600 mg capsules (E-Lyte™ Butyrate, E-Lyte, Inc., Millville, N.J. USA). The patient preferably receives a twice daily oral administration of 3 grams (five 600 mg capsules). Alternatively, butyrate is given as a salt of phenylbutyrate, preferably sodium phenylbutyrate (e.g., from about 8 to about 12 grams daily orally and/or intravenously). Sodium phenylbutyrate is available from Medaus Pharmacy (Birmingham, Ala. USA) as tablets, capsules or liquid.

In a preferred embodiment, a subject treated according to the present methods also receives an effective amount of an oral electrolyte composition. Oral electrolyte compositions are well-known to medical science, and are utilized to supplement the body with mineral salts. The oral electrolyte composition preferably contains the major electrolytes, which include sodium ($Na^+$), calcium ($Ca^{++}$), magnesium ($Mg^{++}$), potassium ($K^+$), chloride ($Cl^-$), phosphate ($PO_4^-$), sulfate ($SO_4^-$), and bicarbonate ($HCO_3^-$). An "effective amount" of the oral electrolyte composition is an amount sufficient to provide the minimum daily requirements of the major electrolytes. One such product is E-Lyte™ Balanced Electrolyte, E-Lyte, Inc., Millville, N.J. USA, sold as a liquid concentrate for 1:16 volume dilution with water. The subject may ingest the electrolyte composition in concentrated form, followed by appropriate dilution in water, or may utilize the appropriately diluted form. For the concentrate, the subject may ingest a tablespoon at a time, followed by 1 to 2 ounces of water. The dosage may be repeated throughout the day.

It is also preferable to maintain a subject being treated by the present methods on a low carbohydrate, high protein, high fat diet; e.g., a diet excluding all grains, sugars, fruit, fruit juices and all "below ground" root vegetables. Suitable low carbohydrate, high protein, high fat diets include such well-known diets as Atkins® or the South Beach Diet™ (see, e.g., Atkins RC, *Atkins for Life*, St. Martins Press, NY, 2003 and Agatston A, *The South Beach Diet: The Delicious Doctor-Designed, Foolproof Plan for Fast and Healthy Weight Loss*, Random House, N.Y., 2003, the entire disclosures of which are herein incorporated by reference).

In a particularly preferred embodiment, the present methods comprise treating a subject who has been diagnosed with ALS, or who is at risk for developing ALS, for an indefinite period of time (e.g., five weeks or more) by: (1) intravenous administration of a PC composition comprising about 0.5 grams phosphatidylcholine, followed by intravenous administration of from about 1.8 to about 2.4 grams of glutathione, twice daily for a minimum of 3 days in a seven-day period; (2) once or twice daily oral administration of a PC composition comprising from about 3.6 to about 7.2 grams of phosphatidylcholine; (3) once daily oral administration of an effective amount of one or more mineral compositions, (the effective amount of the one or more mineral compositions can be doubled or tripled); and (4) once daily oral administration of from about 30 mls to about 60 mls (about 2 to about 4 tablespoons) of an EFA 4:1 composition. In a preferred embodiment, the treatment method further includes: (5) once or twice daily oral administration of from about 3 to about 6 grams of one or more butyrate compounds; and (6) a daily effective amount of an oral electrolyte composition.

Effective amounts of one or more PC compositions, one or more EFA 4:1 compositions and one or more mineral compositions as described above can each be formulated into pharmaceutical compositions (which are also called "medicaments") for treating ALS or for delaying the onset of ALS symptoms in a subject. As used herein, a "pharmaceutical composition" includes compositions for human and veterinary use. Pharmaceutical compositions for parenteral (e.g., intravascular) administration are characterized as being sterile and pyrogen-free. One skilled in the art can readily prepare pharmaceutical compositions of the invention for enteral or parenteral use, for example by using the principles set forth in *Remington's Pharmaceutical Science*, 18th edit. (Alphonso Gennaro, ed.), Mack Publishing Co., Easton, Pa., 1990.

Because phosphatidylcholine, linoleic acid and alpha linolenic acid are both soluble in oils or lipids, the one or more PC compositions and the one or more EFA 4:1 compositions can be conveniently formulated into a single pharmaceutical composition. Thus, in one embodiment, the invention provides a single-dose pharmaceutical composition comprising a PC composition and an EFA 4:1 composition.

The one or more mineral compositions are typically not oil or lipid soluble, and are therefore generally not formulated into a single pharmaceutical composition with the PC compositions and EFA 4:1 compositions, but are rather formulated as separate pharmaceutical compositions. However, the one or more mineral compositions, the one or more PC compositions and the one or more EFA 4:1 compositions can be formulated into a single pharmaceutical composition as an emulsion, for example, an oil-in-water emulsion or water-in-oil emulsion.

The pharmaceutical compositions of the invention can each be in a form suitable for oral use, according to any technique suitable for the manufacture of oral pharmaceutical compositions as are within the skill in the art. For example, the one or more PC compositions and the one or more EFA 4:1 compositions can be formulated (either separately or together) into soft capsules, oily suspensions, or emulsions, optionally in admixture with pharmaceutically acceptable excipients. Suitable excipients for a PC composition or EFA 4:1 composition comprise oil-based media; e.g., archis oil, liquid paraffin, or vegetable oils such as olive oil.

The one or more mineral compositions can be formulated into liquid or solid pharmaceutical compositions, such as aqueous solutions, aqueous or oily suspensions, syrups or elixirs, emulsions, tablets, dispersible powders or granules, hard or soft capsules, optionally in admixture with pharmaceutically acceptable excipients. Suitable excipients for liquid formulation include water or saline, suspending agents such as sodium carboxymethylcellulose, methylcellulose, hydroxypropylmethyl-cellulose, sodium alginate, polyvinylpyrrolidone, gum tragacanth, and gum acacia; dispersing or wetting agents such as lecithin, condensation products of an alkylene oxide with fatty acids (e.g., polyoxyethylene stearate), condensation products of ethylene oxide with long chain aliphatic alcohols (e.g., heptadecethyleneoxy-cetanol), condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyoxyethylene sorbitan monooleate). Suitable excipients for solid formulations include calcium carbonate, sodium carbonate, lactose, calcium phosphate, or sodium phosphate; granulating and disintegrating agents such as maize starch, or alginic acid; binding agents such as starch, gelatin, or acacia; and lubricating agents such as magnesium stearate, stearic acids, or talc, and inert solid diluents such as calcium carbonate, calcium phosphate, or kaolin.

Oral pharmaceutical compositions of the invention can also contain one or more agents selected from the group consisting of sweetening agents, flavoring agents, coloring agents, and preserving agents in order to provide a pharmaceutically elegant and palatable preparation.

Liquid formulations according to the invention can also contain one or more preservatives such as ethyl, n-propyl, or p-hydroxy benzoate; one or more coloring agents; one or more flavoring agents; or one or more sweetening agents such as sucrose, saccharin, or sodium or calcium cyclamate.

Liquid pharmaceutical formulations according to the invention, especially those comprising a PC composition or EFA 4:1 composition, can also contain antioxidants such as tocopherol, sodium metabisulphite, butylated hydroxytoluene (BHT), butylated hydroxyanisole (BHA), ascorbic acid or sodium ascorbate.

The pharmaceutical compositions of the invention can also be in the form of a sterile, pyrogen-free preparations suitable for parenteral administration, for example as a sterile injectable aqueous solution, a suspension or an emulsion. Such pharmaceutical compositions can be formulated using the excipients described above for liquid formulations. For example, a sterile injectable preparation according to the invention can comprise a sterile injectable solution, suspension or emulsion in a non-toxic, parenterally-acceptable diluent or solvent; e.g., as a solution in 1,3-butane diol, water or saline solution. Formulation of sterile, pyrogen-free pharmaceutical compositions suitable for parenteral administration are within the skill in the art.

The invention further provides a kit for the treatment of ALS or for delaying the onset of ALS symptoms. The kit comprises instructions for treating ALS in a subject, or for delaying the onset of ALS symptoms in a subject, and optionally comprises one or more of the following components: 1) one or more PC compositions; 2) one or more EFA 4:1 compositions; and 3) one or more mineral compositions. The kit also optionally comprises one or more butyrate compounds and/or an electrolyte composition. The latter is preferably present in concentrated form. If a particular component is not included in the kit, the kit can optionally comprise information on where to obtain the missing component, for example an order form or uniform resource locator for the internet specifying a website where the component can be obtained.

The instructions provided with the kit describe the practice of the methods of the invention as described above, and optionally describe how to diagnose ALS or identify ALS in a subject, or how to determine if a subject is at risk for developing ALS.

The invention will now be illustrated with the following non-limiting examples.

EXAMPLES

Techniques Used

E-Lyte mineral taste test—This test determines mineral deficiency using a taste test for eight different minerals in liquid form (as a water solution): potassium phosphate; zinc sulphate; magnesium chloride; copper sulfate; potassium chromate; potassium permanganate or manganese gluconate; ammonium molybdate; and selenium selenite. Liquid mineral preparation for the test are available as E-Lyte Liquid Mineral™ set #1-9 (separate solutions of biologically available potassium, zinc, magnesium, copper, chromium, manganese, molybdenum, selenium and iodine), from E-Lyte, Inc. (Millville, N.J. USA). Liquid #9 is not included in the taste test, but is preferably included in a daily mineral composition according to the present invention, as described above. To carry out the taste test, a portion of each liquid is poured into a small cup, starting with liquid #1. Using about 2-3 teaspoons, each liquid is placed in the mouth of the patient. The patient should be instructed to swish the liquid in his/her mouth to obtain a taste response. The taste response is scored on a 1-7 scale: (1) sweat; (2) pleasant; (3) no taste; (4) a taste ("I taste something"), but the taste is neither pleasant nor disturbing, and is not just the taste of plain water; (5) a taste detected, which is not unpleasant, but could be avoided; (6) a disliked taste; and (7) a bad taste. A score of (1) or (2) indicates a deficiency toward the administered mineral, with (1) being very deficient. A score of (3) also indicates need, while a score of (4) indicates a lack of need. A score of (5) indicates that the administered mineral could be avoided, a score of (6) or (7) indicates that the mineral is in excess, and should be avoided at this time.

A portion of each of the minerals scoring between (1) and (4) is given to the patient, preferably together with an acidic juice (orange, grapefruit or pineapple), or with ¼ teaspoon of vitamin C powder.

Intravenous administration of PC compositions—A butterfly catheter with a 23-gauge needle was inserted into a vein the antecubital region of one of the subject' arms. A syringe containing the PC composition 5 to 10 cc total volume was connected to the catheter by a flexible tube. A volume of blood equal to the total volume of the PC composition was drawn into the syringe and the syringe was gently agitated to mix the blood and PC composition. The blood/PC composition mixture was then infused (or "pushed") into the subject over a period of two to five minutes.

Intravenous administration of glutathione—The contents of a syringe containing 9 to 15 cc of a mixture of equal volumes of sterile water was infused (or "pushed") into the subject through the catheter over a period of two to five minutes.

Nine subjects diagnosed with ALS (see Table 2) were treated according to the following ALS Treatment Protocol: (1) intravenous administration of 500 mg Essentiale N™ phosphatidylcholine (A. Natterman & Cie, GmbH, Cologne, Germany), followed by intravenous administration of 1.8 to 2.4 grams of glutathione, twice daily for 3 days in a seven-day period; (2) once daily oral administration of four to eight capsules (900 mg phosphatidylcholine each) of Nutrasal™ PC (Nutrasal LLC, Oxford, Conn. USA) or E-Lyte PhosChol™ (E-Lyte, Inc., Millville, N.J. USA); (3) once or twice daily oral administration of five 600 mg calcium magnesium butyrate capsules (E-Lyte, Inc., Millville, N.J., USA); (4) once daily oral administration of triple portions of various minerals from the E-Lyte Liquid Mineral™ set #1-8 (E-Lyte, Inc., Millville, N.J. USA), as determined by the E-Lyte mineral taste test protocol described above; and (5) once or twice daily oral administration of 30 ml to 60 ml (about 2 to about 4 tablespoons) BodyBio Balance 4:1™ EFA oil (E-Lyte, Inc., Millville, N.J. USA). The subjects were evaluated daily for any improvement in ALS symptoms. The subjects were also kept on a low carbohydrate, high protein, high fat diet; e.g., a diet excluding all grains, sugars, fruit, fruit juices and all "below ground" root vegetables. All "above ground" root vegetables were permitted in the diet.

TABLE 2

Clinical Characteristics of Subjects Diagnosed with ALS

| Case Study | ALS Type | Age | Gender | Time of Onset or Diagnosis | Treatment Duration | Symptoms at Presentation | Symptoms After Treatment |
|---|---|---|---|---|---|---|---|
| 1 | Lower Motor | 48 | Male | October 2002 | 4 weeks | Unable to walk or move arms, hands were clawed, and speech was slurred | Standing and walking unassisted |
| 2 | Lower Motor | 36 | Male | May 2003 | 2 weeks | Slurred speech, gait disturbance, fasciculations, loss | Speech, gait and breathing had remarkably improved |

TABLE 2-continued

Clinical Characteristics of Subjects Diagnosed with ALS

| Case Study | ALS Type | Age | Gender | Time of Onset or Diagnosis | Treatment Duration | Symptoms at Presentation | Symptoms After Treatment |
|---|---|---|---|---|---|---|---|
| | | | | | | of strength in both hands, labored breathing and fatigue | |
| 3 | Lower Motor | 40 | Female | August 2000 | 9 weeks | On ventilator, tube fed, and unable to move | Turn wrist, move elbow, lift shoulder, able to breathe on her own w/out ventilator for 15 mins., and able to get out of bed and sit in a wheelchair |
| 4 | Lower Motor | 58 | Female | April 2003 | 2 weeks | In wheelchair | No longer required wheel chair; walk with cane[1] |
| 5 | Upper Motor | 58 | Male | June 2001 | 2 weeks | Muscle atrophy, gait disturbance, muscle spasm, fasciculations, fatigue, cold intolerance, tremors, shortness of breath, restricted movement in turning neck tapping fingers, lifting arms | Lift, rotate and freely move arms, cross legs, full rotation of neck, gait, fasciculations, fatigue, and tremors much improved. |
| 6 | Upper Motor | 55 | Male | January 2001 | 6 days | Right foot drop, fasciculations, shortness of breath, tinnitus, muscle atrophy, abnormal gait, insomnia, poor coordination, difficulty holding up head, fatigue upon chewing food. | Free movement in fingers, no longer fatigued with chewing, able to hold up head without difficulty for prolonged periods, more fluidity of movement overall, increased facial expression, gait improved, breathing less labored |
| 7 | Lower Motor | 30 | Male | October 2000 | 6 days | In wheelchair, unable to use hands, unable to hold up head, severely slurred speech, fasciculations | Hold up head, movement in neck improved, more strength in right arm, able to walk with walker, shifting weight from one foot to the other |
| 8 | Lower Motor | 41 | Male | April 2003 | 3 weeks | In wheelchair w/ fatigue, fasciculations, poor balance, muscle spasm, numbness in extremities, depression, muscle atrophy, tremor, cold intolerance, unable to lift arms or move hands, wheelchair bound | Able to stand, balance improved, able to lift arms, fasciculations, tremor and muscle spasm resolved. |
| 9 | Familial | 48 | Male | August 1994 | 3 weeks | Loss of balance requiring use of cane, fatigue, shortness of breath, weakness in legs/arms/hands, poor coordination, mood swings; vertigo, blurred vision, spasticity, muscle spasm, fasciculations, muscle weakness. | Able to jump, twirl, walk a straight line and dance. Mood is stable, vision has cleared, breathing less labored, vertigo, spasticity and fasciculations resolved. |

[1]After several months of further treatment, Subject 4 began walking without a cane. The subject had more energy, and her brain fog cleared. A tingling in right foot ceased. Muscle cramps and fasciculations were resolved.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

We claim:

1. A method of treating ALS in a subject who has been diagnosed with ALS, the method consisting of:
   (1) intravenous administration of a PC composition consisting essentially of 0.5 grams of phosphatidylcholine, followed by intravenous administration of 1.8 grams to 2.4 grams of glutathione, twice daily for 3 days in a seven day period;
   (2) once daily oral administration of a PC composition consisting essentially of 3.6 grams to 7.2 grams of phosphatidylcholine;
   (3) once or twice daily oral administration of 3 grams to 6 grams of calcium magnesium butyrate;
   (4) once daily oral administration of triple portions of various minerals selected from potassium, magnesium, calcium, iron, zinc, copper, chromium, manganese, molybdenum, selenium, iodine, or combinations thereof; and
   (5) once or twice daily oral administration of 30 ml to 60 ml of an EFA composition consisting essentially of linoleic acid and alpha-linolenic acid in a ratio of 4:1;
   wherein the severity of at least one ALS symptom is lessened.

* * * * *